United States Patent
Dorian et al.

(10) Patent No.: US 11,541,388 B2
(45) Date of Patent: Jan. 3, 2023

(54) APPARATUS AND METHODS FOR SEPARATING BLOOD COMPONENTS

(71) Applicant: Hanuman Pelican, Inc., New Orleans, LA (US)

(72) Inventors: Randy Dorian, San Diego, CA (US);
Michael D. Leach, Warsaw, IN (US);
Richard W. Storrs, Berkeley, CA (US);
Scott R. King, New Orleans, LA (US)

(73) Assignee: Hanuman Pelican, Inc., New Orleans, LA (US)

( * ) Notice: Subject to any disclaimer, the term of this patent is extended or adjusted under 35 U.S.C. 154(b) by 90 days.

(21) Appl. No.: 17/332,728

(22) Filed: May 27, 2021

(65) Prior Publication Data

US 2021/0283600 A1    Sep. 16, 2021

Related U.S. Application Data

(62) Division of application No. 16/454,525, filed on Jun. 27, 2019, now Pat. No. 11,478,787.

(Continued)

(51) Int. Cl.
*B01L 3/00* (2006.01)
*B04B 5/04* (2006.01)
(Continued)

(52) U.S. Cl.
CPC .......... *B01L 3/50215* (2013.01); *A61K 8/983* (2013.01); *A61K 35/16* (2013.01);
(Continued)

(58) Field of Classification Search
CPC ................ B01L 3/50215; B01L 3/505; B01L 2300/042; B01L 2300/0832;
(Continued)

(56) References Cited

U.S. PATENT DOCUMENTS 2,889,848 A    6/1959  Redmer
3,774,454 A    11/1973 Shaw
(Continued)

FOREIGN PATENT DOCUMENTS

EP    0744026    11/2001
EP    3020481    5/2016
(Continued)

OTHER PUBLICATIONS

Wardlaw SC, Levine RA. Quantitative Buffy Coat Analysis: A New Laboratory Tool Functioning as a Screening Complete Blood Cell Count. JAMA. 1983;249(5):617-620. doi: 10.1001/jama.1983.03330290039026 (Year: 1983).

*Primary Examiner* — Liam Royce
(74) *Attorney, Agent, or Firm* — Levine Bagade Han LLP

(57) ABSTRACT

Apparatus and methods for separating blood components are disclosed in which an apparatus for separating blood generally includes a tube defining a channel and configured for receiving a quantity of blood and a float contained within the tube and having a density which is predefined so that the float is maintained at equilibrium between a first layer formed from a first fractional component of the blood and a second layer formed from a second fractional component of the blood. Upon completion of the centrifugation, the first layer may be removed from the tube while the float isolates the second layer from the first layer.

18 Claims, 14 Drawing Sheets

Related U.S. Application Data

(60) Provisional application No. 62/695,631, filed on Jul. 9, 2018.

(51) Int. Cl.

| | | |
|---|---|---|
| *B01D 21/26* | (2006.01) | |
| *A61K 35/16* | (2015.01) | |
| *A61K 35/19* | (2015.01) | |
| *A61Q 7/00* | (2006.01) | |
| *A61Q 19/08* | (2006.01) | |
| *A61K 8/98* | (2006.01) | |

(52) U.S. Cl.
CPC .............. *A61K 35/19* (2013.01); *A61Q 7/00* (2013.01); *A61Q 19/08* (2013.01); *B01D 21/262* (2013.01); *B01L 3/505* (2013.01); *B04B 5/0414* (2013.01); *B01L 2300/042* (2013.01); *B01L 2300/0832* (2013.01); *B01L 2300/123* (2013.01); *B01L 2300/16* (2013.01)

(58) Field of Classification Search
CPC ........... B01L 2300/123; B01L 2300/16; B01D 21/262; B04B 5/0414
See application file for complete search history.

(56) References Cited

U.S. PATENT DOCUMENTS

| | | | |
|---|---|---|---|
| 3,814,248 | A | 6/1974 | Lawhead |
| 5,393,674 | A | 2/1995 | Levine et al. |
| 5,560,830 | A | 10/1996 | Coleman et al. |
| 5,707,876 | A | 1/1998 | Levine |
| 6,123,655 | A | 9/2000 | Fell |
| 6,465,256 | B1 | 10/2002 | Iskra |
| 7,074,577 | B2 | 7/2006 | Haubert et al. |
| 7,077,273 | B2 | 7/2006 | Ellsworth et al. |
| 7,153,477 | B2 | 12/2006 | DiCesare et al. |
| 7,179,391 | B2 | 2/2007 | Leach et al. |
| 7,223,346 | B2 | 5/2007 | Dorian et al. |
| 7,329,534 | B2 | 2/2008 | Haubert et al. |
| 7,358,095 | B2 | 4/2008 | Haubert et al. |
| 7,374,678 | B2 | 5/2008 | Leach et al. |
| 7,445,125 | B2 | 11/2008 | Ellsworth et al. |
| 7,470,371 | B2 | 12/2008 | Dorian et al. |
| 7,771,590 | B2 | 8/2010 | Leach et al. |
| 7,780,860 | B2 | 8/2010 | Higgins et al. |
| 7,837,884 | B2 | 11/2010 | Dorian et al. |
| 7,845,499 | B2 | 12/2010 | Higgins et al. |
| 7,947,236 | B2 | 5/2011 | Losada et al. |
| 7,992,725 | B2 | 8/2011 | Leach et al. |
| 8,012,742 | B2 | 9/2011 | Haubert et al. |
| 8,048,297 | B2 | 11/2011 | Leach et al. |
| 8,048,321 | B2 | 11/2011 | Leach et al. |
| 8,119,013 | B2 | 2/2012 | Leach et al. |
| 8,177,072 | B2 | 5/2012 | Chapman et al. |
| 8,187,477 | B2 | 5/2012 | Dorian et al. |
| 8,236,258 | B2 | 8/2012 | Leach et al. |
| 8,328,024 | B2 | 12/2012 | Leach et al. |
| 8,348,066 | B2 | 1/2013 | Ellsworth |
| 8,377,395 | B2 | 2/2013 | Coleman |
| 8,394,342 | B2 | 3/2013 | Felix et al. |
| 8,445,264 | B2 | 5/2013 | Seubert et al. |
| 8,474,630 | B2 | 7/2013 | Dorian et al. |
| 8,506,823 | B2 | 8/2013 | Chapman et al. |
| 8,511,479 | B2 | 8/2013 | Chapman et al. |
| 8,511,480 | B2 | 8/2013 | Chapman et al. |
| 8,518,272 | B2 | 8/2013 | Hoeppner |
| 8,596,470 | B2 | 12/2013 | Leach et al. |
| 8,603,345 | B2 | 12/2013 | Ross et al. |
| 8,603,346 | B2 | 12/2013 | Leach et al. |
| 8,632,736 | B2 | 1/2014 | Spatafore et al. |
| 8,632,740 | B2 | 1/2014 | Dastane et al. |
| 8,747,781 | B2 | 6/2014 | Bartfield et al. |
| 8,794,452 | B2 | 8/2014 | Crawford et al. |
| 8,808,551 | B2 | 8/2014 | Leach et al. |
| 8,950,586 | B2 | 2/2015 | Dorian et al. |
| 8,992,862 | B2 | 3/2015 | Leach et al. |
| 8,998,000 | B2 | 4/2015 | Crawford et al. |
| 9,011,800 | B2 | 4/2015 | Leach et al. |
| 9,079,123 | B2 | 7/2015 | Crawford et al. |
| 9,114,334 | B2 | 8/2015 | Leach et al. |
| 9,120,095 | B2 | 9/2015 | O'Connel, Jr. |
| 9,138,664 | B2 | 9/2015 | Leach et al. |
| 9,162,232 | B2 | 10/2015 | Ellsworth |
| 9,239,276 | B2 | 1/2016 | Landrigan et al. |
| 9,272,083 | B2 | 3/2016 | Duffy et al. |
| 9,333,445 | B2 | 5/2016 | Battles et al. |
| 9,339,741 | B2 | 5/2016 | Newby et al. |
| 9,364,828 | B2 | 6/2016 | Crawford et al. |
| 9,375,661 | B2 | 6/2016 | Chapman et al. |
| 9,393,575 | B2 | 7/2016 | Ellsworth et al. |
| 9,393,576 | B2 | 7/2016 | Ellsworth et al. |
| 9,399,226 | B2 | 7/2016 | Ellsworth et al. |
| 9,452,427 | B2 | 9/2016 | Felix et al. |
| 9,642,956 | B2 | 5/2017 | Landrigan et al. |
| 9,649,579 | B2 | 5/2017 | Leach et al. |
| 9,656,274 | B2 | 5/2017 | Ellsworth et al. |
| 9,694,359 | B2 | 7/2017 | Losada et al. |
| 9,700,886 | B2 | 7/2017 | Felix et al. |
| 9,714,890 | B2 | 7/2017 | Newby et al. |
| 9,731,290 | B2 | 8/2017 | Crawford et al. |
| 9,802,189 | B2 | 10/2017 | Crawford et al. |
| 9,897,589 | B2 | 2/2018 | Woodell-May |
| 9,919,307 | B2 | 3/2018 | Crawford et al. |
| 9,919,308 | B2 | 3/2018 | Crawford et al. |
| 9,919,309 | B2 | 3/2018 | Crawford et al. |
| 9,933,344 | B2 | 4/2018 | Newby et al. |
| 9,937,445 | B2 | 4/2018 | King et al. |
| 10,005,081 | B2 | 6/2018 | Duffy et al. |
| 10,183,042 | B2 | 1/2019 | Leach et al. |
| 10,343,157 | B2 | 7/2019 | Crawford et al. |
| 10,350,591 | B2 | 7/2019 | Felix et al. |
| 10,376,879 | B2 | 8/2019 | Crawford et al. |
| 10,393,728 | B2 | 8/2019 | Woodell-May |
| 10,413,898 | B2 | 9/2019 | Crawford et al. |
| 10,456,782 | B2 | 10/2019 | Crawford et al. |
| 10,603,665 | B2 | 3/2020 | Levine et al. |
| 10,618,044 | B1 | 4/2020 | Petrie, Jr. |
| 2003/0205538 | A1 | 11/2003 | Dorian et al. |
| 2007/0034579 | A1 | 2/2007 | Dorian et al. |
| 2012/0308447 | A1 | 12/2012 | Abrahamson |
| 2014/0287487 | A1 | 9/2014 | Campton |
| 2015/0231626 | A1 | 8/2015 | Shi et al. |
| 2016/0008808 | A1 | 1/2016 | Levine et al. |
| 2016/0041077 | A1 | 2/2016 | U'Ren et al. |
| 2017/0304823 | A1 | 10/2017 | Sparks et al. |
| 2018/0304251 | A1 | 10/2018 | Ellson et al. |
| 2018/0353952 | A1 | 12/2018 | Olson |
| 2020/0009304 | A1 | 1/2020 | Dorian et al. |
| 2020/0009551 | A1 | 1/2020 | Dorian et al. |
| 2020/0009552 | A1 | 1/2020 | Crawford et al. |
| 2020/0129560 | A1 | 4/2020 | Centeno et al. |
| 2020/0197929 | A1 | 6/2020 | Weinstock et al. |
| 2020/0215243 | A1 | 7/2020 | Dorian et al. |
| 2020/0246516 | A1 | 8/2020 | Dorian et al. |
| 2020/0289720 | A1 | 9/2020 | Streit |

FOREIGN PATENT DOCUMENTS

| | | |
|---|---|---|
| EP | 1005909 | 6/2020 |
| WO | WO 2018/197562 | 11/2018 |
| WO | WO 2018/197564 | 11/2018 |
| WO | WO 2018/197592 | 11/2018 |
| WO | WO 2020/013981 | 1/2020 |
| WO | WO 2020/013997 | 1/2020 |
| WO | WO 2020/154305 | 7/2020 |
| WO | WO 2020/163105 | 8/2020 |

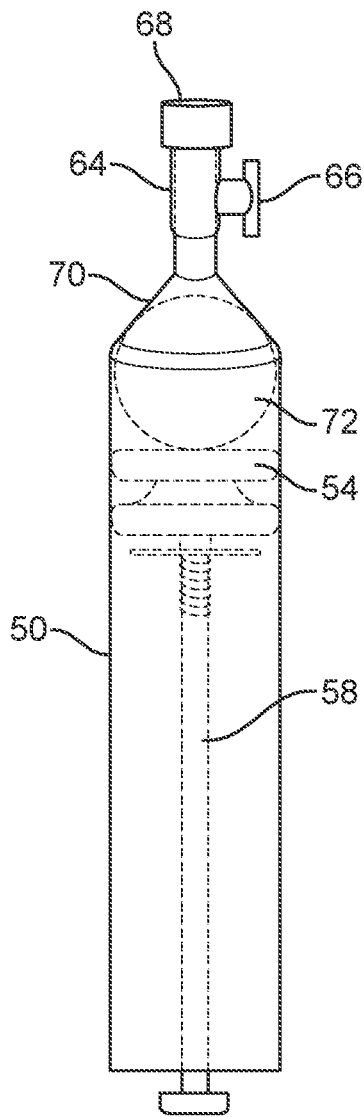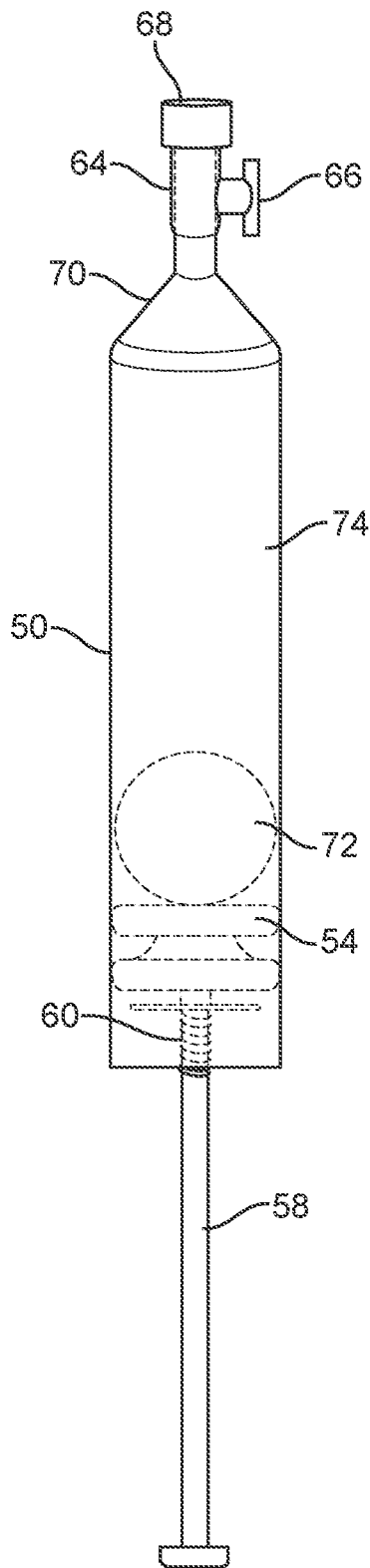
FIG. 4A
FIG. 4B

APPARATUS AND METHODS FOR SEPARATING BLOOD COMPONENTS

CROSS-REFERENCE TO RELATED APPLICATION

This application is a divisional of U.S. patent application Ser. No. 16/454,525 filed Jun. 27, 2019 which claims the benefit of priority to U.S. Prov. 62/695,631 filed Jul. 9, 2018, each of which is incorporated herein by reference in its entirety.

FIELD OF THE DISCLOSURE

The present invention relates to apparatus and methods for separating blood components. More particularly, the present invention relates to apparatus and methods for effectively separating and removing specific components from blood.

BACKGROUND

Blood may be fractionated and the different fractions of the blood used for different medical needs. For instance, anemia (low erythrocyte levels) may be treated with infusions of erythrocytes. Thrombocytopenia (low thrombocyte (platelet) levels) may be treated with infusions of platelet concentrate.

The sedimentation of the various blood cells and plasma is based on the different specific gravity of the cells and the viscosity of the medium. When sedimented to equilibrium, the component with the highest specific gravity (density) eventually sediments to the bottom, and the lightest rises to the top. Under the influence of gravity or centrifugal force, blood spontaneously sediments into three layers. At equilibrium the top, low-density layer is a straw-colored clear fluid called plasma. Plasma is a water solution of salts, metabolites, peptides, and many proteins ranging from small (insulin) to very large (complement components). Plasma per se has limited use in medicine but may be further fractionated to yield proteins used, for instance, to treat hemophilia (factor VIII) or as a hemostatic agent (fibrinogen). The term platelet rich plasma (PRP) is used for this component because most of the plasma proteins and platelets in the whole blood are in the plasma following slow centrifugation so the concentration of platelets in the plasma has increased while suspended in supernatant plasma. The uppermost layer after centrifugation typically contains plasma proteins only and is typically called platelet-poor plasma (PPP) due to the absence or low number of platelets as a result of a "hard spin".

The bottom, high-density layer is a deep red viscous fluid comprising nuclear red blood cells (RBC) specialized for oxygen transport. The red color is imparted by a high concentration of chelated iron or heme that is responsible for the erythrocytes high specific gravity. Packed erythrocytes, matched for blood type, are useful for treatment of anemia caused by, e.g., bleeding. The relative volume of whole blood that consists of erythrocytes is called the hematocrit, and in normal human beings can range from about 38% to about 54%.

The intermediate layer is the smallest layer, appearing as a thin white band on top the erythrocyte layer and below the plasma, and is called the buffy coat. The buffy coat itself has two major components, nucleated leukocytes (white blood cells) and a nuclear smaller bodies called platelets (or thrombocytes). Leukocytes confer immunity and contribute to debris scavenging. Platelets seal ruptures in the blood vessels to stop bleeding and deliver growth and wound healing factors to the wound site. The buffy coat may be separated from whole blood when the blood is subjected to a "hard spin" in which the whole blood is spun hard enough and long enough so that platelets sediment from plasma onto packed red cells and white cells percolate up through red cell pack to the interface between red cells and plasma.

When whole blood is centrifuged at a low speed (e.g., up to 1,000 g) for a short time (e.g., two to four minutes) white cells sediment faster than red cells and both sediment much faster than platelets. At higher speeds the same distribution is obtained in a shorter time. The method of harvesting PRP from whole blood is based on this principle. Centrifugal sedimentation that takes the fractionation only as far as separation into packed erythrocytes and PRP is called a "soft spin" which is typically used to describe centrifugation conditions under which erythrocytes are sedimented but platelets remain in suspension. "Hard spin" is typically used to describe centrifugation conditions under which erythrocytes sediment and platelets sediment in a layer immediately above the layer of erythrocytes.

The auto-transfusion equipment used to make autologous platelet concentrates requires a skilled operator and considerable time and expense and these devices require a large prime volume of blood. While many of these devices have somewhat reduced the cost and the time required, skilled operators and time are still required. Accordingly, there remains a need for simple and effective methods and devices for separating and removing components from whole blood. Embodiments of the present invention are designed to meet these and other needs.

SUMMARY

Some embodiments of the present invention relate to apparatus and methods for rapid fractionation of blood into its different components, e.g., erythrocyte, plasma, and platelet fractions. The devices and methods described have particular value for rapid preparation of autologous concentrated platelet fractions, e.g., to help or speed healing.

Whole blood may be spun in a vented tube with a density-adjusted float mechanism which can float freely and unanchored within the tube along with the whole blood. The density of the float mechanism may be adjusted so that when the whole blood has been separated, the float at equilibrium may rest above the sedimented red blood cell (RBC) pack, isolating the PRP supernatant. The float may serve as a barrier to prevent contamination with RBC when the PRP is withdrawn from the tube.

One variation may generally comprise a separator assembly which may include a syringe or centrifuge container tube which defines a channel for collecting, e.g., a whole blood sample. The separator float may have an atraumatic and arcuate shape, e.g., spherical, ellipsoidal, cylindrical, etc. and having a diameter which corresponds to the inner diameter of the channel so that the float may move freely within the length of the channel uninhibited and which allows for blood components to pass through the annular space defined between the outer diameter of the float and the inner surface of the channel. However, this annular space may also be small enough so as to discourage the free and uninhibited passage of blood components through.

A float having a spherical shape not only can be used to isolate the upper and lower fluid fractions, but may also decrease the likelihood of the float cocking or jamming during centrifugation. Additionally and/or optionally, select surfaces or all of the surfaces of the float may also be optionally treated as well. For instance, overmold skins, silicone coatings, wetting agents such as latherin, surfactant proteins, etc., may be applied to the select surfaces of the float or over the entirety of the float. In one variation, the upper surface of the float may be treated to trap or retain a thin layer of red blood cells upon which platelets in the PRP layer may sediment upon. The presence of the red blood cells may cushion and minimize any platelets from directly contacting the surface of the float which may potential evert and damage the contacting platelets.

In one variation, the density of the float can be set so that the RBC layer is entirely below the upper surface of the float, e.g., after a "soft spin". Alternatively, the density of the float may be set to capture a small amount of the RBC layer above the float. If the buffy coat is desired, the density of the float can be set so that after a "hard spin" the buffy coat and a small amount of the RBC layers are above the float. The same float may have its density set so that the float resides between the RBC layer and the PRP layer, e.g., at its midline or anywhere along the float, after a soft spin and then resides with, e.g., its midline or anywhere along the float, below the buffy coat after a "hard spin". Some plasma can be withdrawn separately before the buffy coat is harvested to produce a more concentrated final product.

As previously mentioned, the float at equilibrium may rest above the sedimented red blood cell (RBC) pack, isolating the PRP supernatant such as after a "soft spin". The float at equilibrium may accordingly separate the channel between an upper channel in which the PRP layer and/or buffy coat resides above the float (e.g., above the outer diameter of the float) towards a proximal or proximal or upper end of the tube, and a lower channel in which the RBC layer resides below the float (e.g., below the outer diameter of the float) towards a distal or lower end of the tube. In other variations, the density of the float may be tuned so that the buffy coat forms around the periphery of the float, e.g., above the midline of the float or anywhere along the float after a "hard spin". Separating the PRP layer from the RBC layer helps to ensure that the any red blood cells from the RBC layer are entirely isolated from the supernatant PRP layer contained above the float.

In another variation the tube may optionally include a seal to maintain sterility. The seal may also incorporate a withdrawal tube connected to a withdrawal tube channel defined through the seal. The position of the seal relative to the tube may be optionally adjusted so that once processing has been completed and the float is positioned at equilibrium relative to the upper and lower fluid fractions, the seal may be pushed, screwed, or otherwise urged down upon the tube so as to position the opening of the withdrawal tube into contact against or in proximity to the float so that the PRP layer can be withdrawn through the tube.

In another alternative, the float may optionally incorporate a tether attached to the float to facilitate its removal, if needed, while in other variations the tether may be configured from a length of tubing, e.g., silicone tubing, connected or connectable to an opening for removal of the PRP layer. In yet another variation, the relatively high viscosity of the RBC layer may be utilized to maintain separation when the tube is inverted so that the supernatant PRP layer can be withdrawn from a cap or septum Luer on the top cap of the inverted tube. The tube could also be configured to expand radially relative to its longitudinal axis during centrifugation to allow the float to migrate freely within the tube to its equilibrium position relative to the centrifuged fractional layers. However, when the centrifugation is stopped, the inner diameter of the tube may contract to trap the float in place at its equilibrium position. The float itself could alternatively be compressible under centrifugally generated pressure but re-expand after centrifugation has stopped so as to lock a position of the float against the inner surface of the tube at its equilibrium position.

As previously discussed, the float itself may also be in an alternative shape. Another particular variation of the float may comprise a tapered interface surface formed in a conical configuration which terminates in an apex that may be atraumatically shaped, e.g., blunted, so as to minimize damage to the blood components. The tapered interface surface may be optionally shaped so as to mirror the tapered shape of the tube interior. The tapered interface surface may also prevent red blood cells from accumulating upon the upper surface of the float during centrifugation. The tapered interface surface may present a slanted or non-orthogonal surface relative to a normal surface of the float which may facilitate the platelets to move or slide down upon the slanted interface surface. The degree of the slant may range anywhere from, e.g., about 2 to about 45 degrees, although the degree of the non-orthogonal surface may vary depending on factors such as the volume of fluid present. Moreover, the surfaces may be smoothed from a relatively rough polymer to a polished surface, e.g., utilizing polymer coatings, nanoparticles, etc. Additionally and/or alternatively, a bottom surface of the float may also be tapered as well so as to prevent platelets from depositing upon the lower surface as the red blood cells pack out, squeezing platelets out of the burgeoning pack.

In yet another variation, a syringe or container tube may be used in a vacuum-drawn system for separating and then collecting the supernatant fraction. A translatable plunger may be slidably positioned within the channel and a pull rod may be coupled to the plunger via a plunger lock attached to the plunger on a side of the plunger opposite to the float. A pull rod lock may be integrated with the tube at a distal surface of the tube around a pull rod opening through which the pull rod may be translated. A Luer assembly may be integrated with at a proximal end of the tube along with a valve and a cap or septum Luer which may be used to seal the Luer.

The proximal end of the tube just below the Luer assembly may also define an interface surface which may be tapered or shaped to receive the float in a corresponding manner to optimize the amount of the PRP layer which may be withdrawn from the tube.

One variation for utilizing the container tube may utilize the pull rod which may be pushed to move the plunger and float into an initial position where the float is pushed into contact against the interface surface of tube prior to receiving whole blood. The tube may be supplied preloaded with, e.g., anticoagulant or any other agent, contained within the channel. Having the tube preloaded with anticoagulant would enable the blood to be drawn directly into the tube without the need for additional processing. With the valve closed, the pull rod may be pulled or pushed to move the plunger into a distal position within the tube. Because the valve is closed, a vacuum may be formed within the tube. The pull rod may be rotated partially about its longitudinal axis relative to the tube and plunger so as to lock a position of the pull rod to the tube and to prevent the plunger from being moved back proximally in position due to the vacuum.

A syringe or blood line may be attached to the Luer and the valve may then be opened allowing (whole) blood to be drawn through the Luer and into the channel by the vacuum formed within the tube. Once the blood has filled the channel of tube, the valve may then be closed again and the blood line disconnected and removed. The pull rod may be decoupled or detached from the plunger lock as well as from the pull rod lock such that the pull rod is fully removed so that the tube, float, and whole blood may be centrifuged. With the whole blood introduced within the channel or tube, the float may remain settled at its distal position prior to centrifuging the assembly.

Once the tube and its contents have been sufficiently centrifuged, the whole blood may separate into its fractional components and the float may alter its position within the channel accordingly due to the differing densities of the individual fractional layers. To effect removal of the PRP layer, a syringe or line may be coupled to the Luer and the valve may then be opened to allow withdrawal of the PRP layer through line. The RBC layer may remain between the plunger and float and the float may remain at the interface of the PRP layer and RBC layer as the PRP layer is withdrawn through Luer. As the PRP layer is fully withdrawn the upper surface of the float may come into contact against the interface surface of the tube so that the float and interface surface form a float interface which may seal the tube and prevent any further withdrawal through Luer. The RBC layer may accordingly remain trapped between the lower surface of the float and the plunger.

For shipment and storage of the tube, the float may incorporate an attractive element such as a magnet embedded entirely or partially within the float. An externally positioned attractive element may be located externally of the tube, such as near the bottom of the tube, to attract the embedded element within the float to prevent the float from movement during shipment or handling of the tube. Prior to use of the tube, the external attractive element may be removed to release a position of the float within the tube.

In yet another variation, an external clamp on the tube may be used to trap the position of the float at the bottom of the tube to ensure that the float remains secured in its position particularly if any preloaded anticoagulant is present within the tube. The clamp may be removed before or after blood introduction or before centrifugation.

In one variation, an apparatus for separating blood may generally comprise a tube defining a channel and configured for receiving a quantity of blood, and a float contained within the tube and having a density which is predefined so that the float is maintained at equilibrium between a first layer formed from a first fractional component of the blood and a second layer formed from a second fractional component of the blood.

In another variation, a method for separating blood may generally comprise introducing a volume of blood into a channel of a tube which encloses a float having a density which is predefined, and subjecting the tube to a centrifugation such that the blood separates into at least a first layer formed from a first fractional component of the blood and a second layer formed from a second fractional component of the blood, wherein the float is maintained at equilibrium between the first layer and the second layer.

BRIEF DESCRIPTION OF THE DRAWINGS

FIGS. 4A to 4G show an example of the float separator assembly used to separate and selectively collect the different blood components.

DETAILED DESCRIPTION

Throughout the description, terms such as "top", "above, "bottom", "below" are used to provide context with respect to the relative positioning of components when, e.g., a container tube with fractional components of blood are positioned when the longitudinal axis of a container tube is positioned upright or non-horizontally. Such description is used for illustrative purposes only.

In one variation of a separator assembly, whole blood may be spun in a vented tube with a density-adjusted float mechanism which can float freely and unanchored within the tube along with the whole blood. The density of the float mechanism may be defined or predefined using various methodologies, e.g., combining differing polymers in differing ratios, integrating weights, removing mass, etc., so that when the whole blood has been separated, the float at equilibrium may rest above the sedimented red blood cell (RBC) pack, isolating the PRP supernatant. The float may serve as a barrier to prevent contamination with RBC when the PRP is withdrawn from the tube.

Figure 1A:
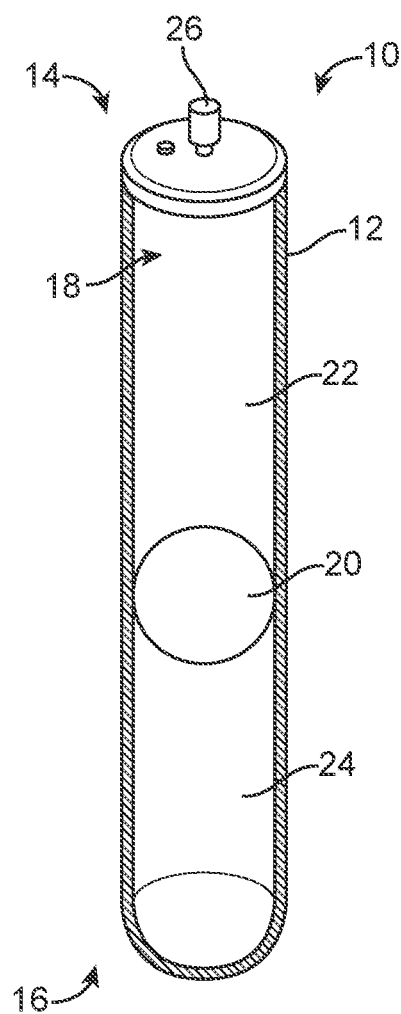
FIG. 1A shows a perspective of one variation of a float separator assembly.

One variation is shown in the perspective view of FIG. 1A which shows a separator assembly 10 which may generally comprise a syringe or centrifuge container tube 12 which defines a channel 18 for collecting, e.g., a whole blood sample. The container tube 12 may be made of any variety of biocompatible materials and may also generally range in dimensions but in one example may have an inner diameter of, e.g., 1.5 to 3.5 cm, with a length of, e.g., 6 to 12 cm. The separator float 20 may have an atraumatic and arcuate shape, e.g., spherical, ellipsoidal, cylindrical, etc. and having a diameter which corresponds to the inner diameter of the channel 18 so that the float 20 may move freely within the length of the channel 18 uninhibited and which allows for blood components to pass through the annular space defined between the outer diameter of the float 20 and the inner surface of the channel 18. However, this annular space may also be small enough so as to discourage the free and uninhibited passage of blood components through. Hence, the outer diameter of the float 20 may range from, e.g., generalized to have an outer diameter of 98 to 101% of the inner surface of the channel 18.

For floats 20 having an outer diameter which equals or exceeds the inner diameter of the channel 18 in which the float 20 is contained when at rest, such floats 20 may be used with container tubes 12 made from flexible materials such as plastics or polymers rather than glass. The inner diameter of the channel 18 may reconfigure itself to radially expand to result in a relatively larger inner diameter, for instance, when spun in a separation procedure. During this spinning process, the float 20 may freely move within the channel 18 to a position of equilibrium relative to the blood components contained within. When the container tube 12 has stopped spinning or has slowed down, the inner diameter of the channel 18 may reconfigure itself to radially retract to a relatively narrower diameter which may then clamp down or compress against the outer diameter of the float 20.

In other variations, the float 20 may have an outer diameter relative to the inner surface of the channel 18 ranging from tens or hundreds of microns of clearance (or interference), depending on the particular application.

The variation shown in FIG. 1A illustrates a float 20 having a spherical shape which not only can be used to isolate the upper and lower fluid fractions, but may also decrease the likelihood of the float 20 cocking or jamming during centrifugation. The float 20 may also be fabricated from any variety of biocompatible materials so long as the density of the float 20 is desirably tuned or tunable for the present application. The float 20 may thus be fabricated as a solid and uniform object (having a suitable density) or in other variations, the float 20 may be hollow so as to be injected or filled with a material which allows for the float 20 density to be changed or desirably adjusted. In this variation, the separator float 20 may have a density which is tuned specifically for use with whole blood, e.g., specific density of 1.0 to 1.1 gram/ml at 25° C.), while in other variations, the float 20 may be fabricated to have a different density, e.g., 1.03 to 1.07 gram/ml, etc.

Additionally and/or optionally, select surfaces or all of the surfaces of the float 20 may also be optionally treated as well. For instance, overmold skins, silicone coatings, wetting agents such as latherin, surfactant proteins, etc., may be applied to the select surfaces of the float or over the entirety of the float. In one variation, the upper surface of the float 20 may be treated to trap or retain a thin layer of red blood cells upon which platelets in the PRP layer may sediment upon. The presence of the red blood cells may cushion and isolate any platelets from directly contacting the surface of the float 20 which may potentially evert and damage the contacting platelets. In this instance, at least one layer of the red blood cells upon the surface of the float 20 may be sufficient to provide the cushioning to the platelets.

Although the float 20 is shown as having a spherical shape, the float may be shaped to have various configurations. For example, in other embodiments, the float may be shaped to have a cylindrical body having a length and a curved, domed, or otherwise convex shape along the bottom or distal portion of the float. The upper or proximal portion of the float may also be curved, domed, convex, concave, or angled relative to a longitudinal axis of the float.

In one variation, the density of the float 20 can be set so that the RBC layer is entirely below the upper surface of the float 20, e.g., after a "soft spin". Alternatively, the density of the float 20 may be set to capture a small amount of the RBC layer above the float 20. If the buffy coat is desired, the density of the float 20 can be set so that after a "hard spin" the buffy coat and a small amount of the RBC layers are above the float 20. The same float 20 may have its density set so that the float 20 resides between the RBC layer and the PRP layer, e.g., at its midline or anywhere along the float, after a soft spin and then resides with, e.g., its midline or anywhere along the float, below the buffy coat after a "hard spin". Some plasma can be withdrawn separately before the buffy coat is harvested to produce a more concentrated final product.

For discussion purposes, a "hard spin" may range, e.g., between 2000 to 4000×g over 2 to 20 minutes, while a "soft spin" may range, e.g., between 500 to 1000×g over 5 to 20 minutes.

As previously mentioned, the float 20 at equilibrium may rest above the sedimented red blood cell (RBC) pack, isolating the PRP supernatant such as after a "soft spin". The float 20 at equilibrium may accordingly separate the channel 18 between an upper channel 22 in which the PRP layer and/or buffy coat resides above the float 20 (e.g., above the outer diameter of the float 20) towards a proximal or proximal or upper end 14 of the tube 12, and a lower channel 24 in which the RBC layer resides below the float 20 (e.g., below the outer diameter of the float 20) towards a distal or lower end 16 of the tube 12. In other variations, the density of the float 20 may be tuned so that the buffy coat forms around the periphery of the float 20, e.g., above the midline 34 of the float 20 after a "hard spin" or anywhere along the float. Separating the PRP layer from the RBC layer helps to ensure that the any red blood cells from the RBC layer are entirely isolated from the supernatant PRP layer contained above the float 20. The tube 12 may also have a cover or seal and a removable cap or septum Luer 26 through which the PRP layer and/or buffy coat may be accessed for removal. While a cap may be removable to provide access for withdrawal, the use of a septum Luer 26 may enable the septum Luer 26 to remain in place, e.g., for introducing blood into the tube 50.

Alternatively, the tube 12 may be sealed with a conventional septum which omits any Luer fittings. By utilizing a septum to seal the tube 12, the tube 12 may be vacuum sealed until used.

While the density may be tuned to have the float 20 positioned at equilibrium at specified positions between the fractional layers, there is relatively greater latitude on the tolerance for the density as the float 20. For example, if the float 20 were used to separate the intermediate buffy coat layer after a "hard spin", the density tolerance on the float 20 would be much tighter given the relatively thin layer of the buffy coat compared to the PRP or RBC layers. On the other hand, if the float 20 were used to separate the PRP layer from the RBC layer after a "soft spin", the latitude on the density range for the float 20 would be relatively greater.

Figure 1B:
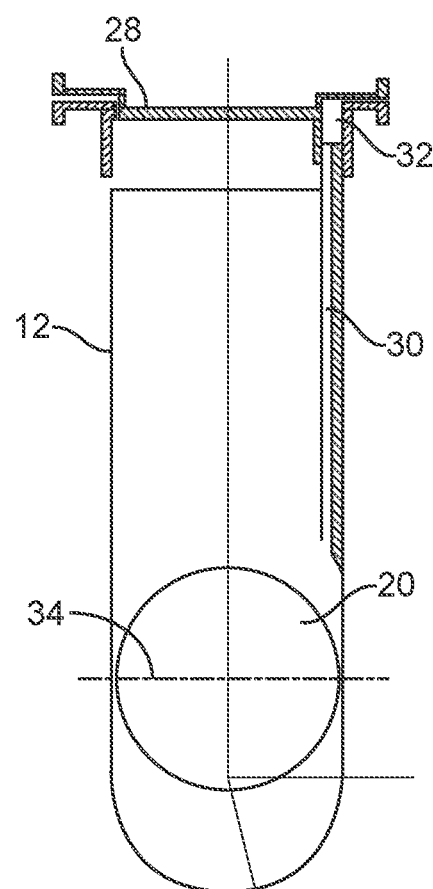
FIG. 1B shows a partial cross-sectional side view another variation of a float separator assembly having a withdrawal tube.

Another variation is shown in the partial cross-sectional side view of FIG. 1B which illustrates a tube 12 having the float 20 within. An example of the float neutral line 34 (e.g., outer diameter) is shown for illustrative purposes. The tube 12 may optionally include a seal 28 to maintain sterility, as described above. The seal 28 may also incorporate a withdrawal tube 30 connected to a withdrawal tube channel 32 defined through the seal 28, as illustrated. The position of the seal 28 relative to the tube 12 may be optionally adjusted so that once processing has been completed and the float 20 is positioned at equilibrium relative to the upper and lower fluid fractions, the seal 28 may be pushed, screwed, or otherwise urged down upon the tube 12 so as to position the opening of the withdrawal tube 30 into contact against or in proximity to the float 20 so that the PRP layer can be withdrawn through the tube 30.

Figure 1C:
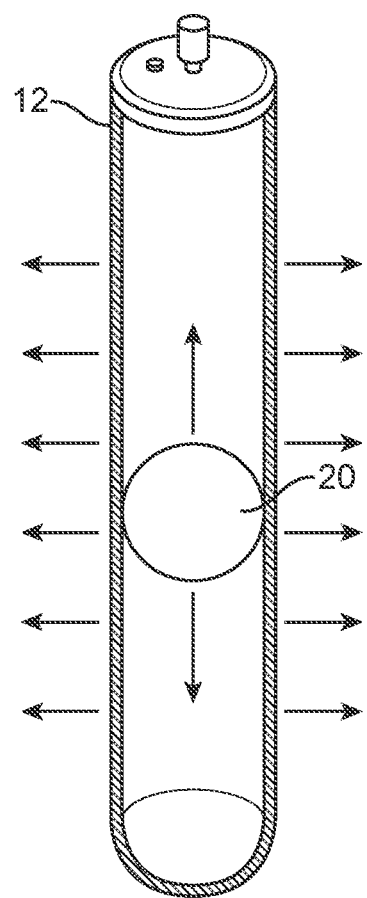
FIGS. 1C and 1D show perspective views of alternative variations for locking a relative position of the float within the tube after centrifugation is completed.
Figure 1D:
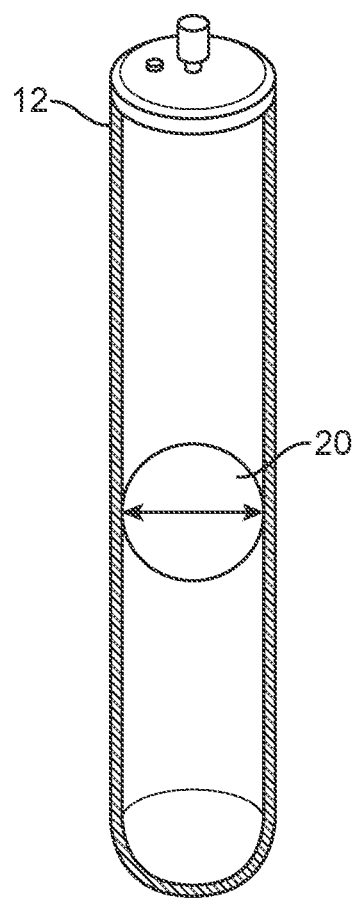

In another alternative, the float 20 may optionally incorporate a tether (not shown) attached to the float 20 to facilitate its removal, if needed, while in other variations the tether may be configured from a length of tubing, e.g., silicone tubing, connected or connectable to an opening for removal of the PRP layer. In yet another variation, the relatively high viscosity of the RBC layer may be utilized to maintain separation when the tube 12 is inverted so that the supernatant PRP layer can be withdrawn from a cap or septum Luer 26 on the top cap of the inverted tube 12. If the viscosity of the RBC layer is insufficient to reliably maintain separation when the tube is inverted, the tube 12 could be configured to expand radially relative to its longitudinal axis during centrifugation to allow the float 20 to migrate freely within the tube 12 to its equilibrium position relative to the centrifuged fractional layers, as illustrated in FIG. 1C. In other words, the tube 12 may expand from a resting first diameter to an expanded second diameter when undergoing centrifugation. The float 20 may have a float diameter which is equal to or slightly larger than the first diameter of the tube 12 but which is less than the expanded second diameter of the tube 12. However, when the centrifugation is stopped, the inner diameter of the tube 12 may contract from its expanded second diameter back down to its first diameter to trap the float 20 in place at its equilibrium position. The float 20 itself could alternatively be compressible under centrifugally generated pressure but re-expand after centrifugation has stopped so as to lock a position of the float 20 against the inner surface of the tube 12 at its equilibrium position, as illustrated in FIG. 1D.

Figure 2A:
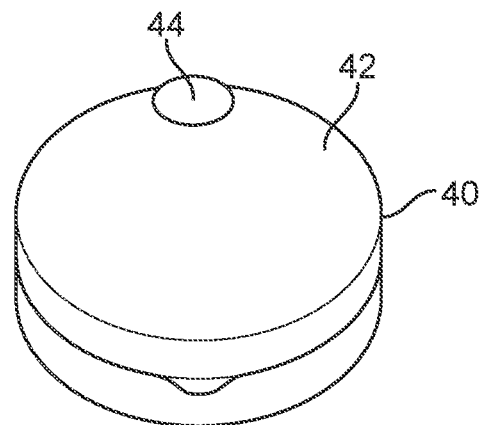
FIGS. 2A and 2B show perspective and side views of another variation of the float separator having an upper tapered interface surface and both upper and lower tapered interface surfaces.
Figure 2B:
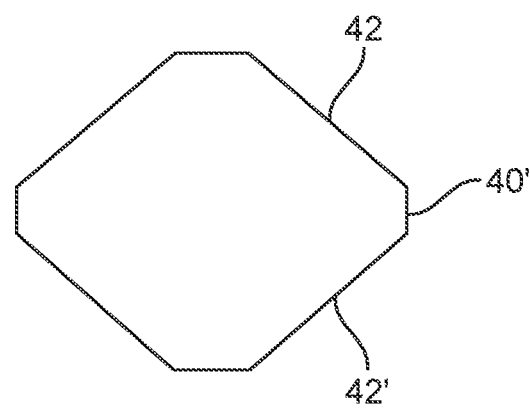

As previously discussed, the float itself may also be in an alternative shape. Another particular variation of the float may be seen in the perspective view of FIG. 2A which illustrates a tapered float 40 having a tapered interface surface 42 formed in a conical configuration which terminates in an apex 44 or in a convex configuration that may be atraumatically shaped, e.g., blunted, so as to minimize damage to the blood components. The tapered interface surface 42 may be optionally shaped so as to mirror the tapered shape of the tube interior. The tapered interface surface 42 may also prevent red blood cells from accumulating upon the upper surface of the float 40 during centrifugation. Additionally and/or alternatively, a bottom surface 42' of the float 40', as shown in the side view of FIG. 2B, may also be tapered as well so as to prevent platelets from depositing upon the lower surface as the red blood cells pack out, squeezing platelets out of the burgeoning pack.

In some embodiments, the degree of the slant may range anywhere from, e.g., about 2 to about 45 degrees, optionally from about 2 to about 40 degrees, from about 2 to about 35 degrees, from about 2 to about 30 degrees, from about 2 to about 25 degrees, from about 2 to about 20 degrees, from about 2 to about 15 degrees, from about 2 to about 10 degrees or from about 2 to about 5 degrees, relative to a normal surface of the float. In some embodiments, the degree of slant may range anywhere from, e.g., from about 2 to about 45 degrees, optionally from about 5 to about 40 degrees, from about 7.5 to about 35 degrees, from about 10 to about 30 degrees, from about 12.5 to about 25 degrees, or from about 15 to about 20 degrees, relative to a normal surface of the float. In other embodiments, the degree of the slant may be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 degrees, relative to a normal surface of the float.

In some embodiments, the float has a surface topography configured to substantially prevent platelet adhesion. In other embodiments, the float is configured to have a surface topography and surface tapered at an angle to substantially prevent platelet adhesion. The present inventors have discovered the optimal relationship between surface topography and taper angle.

Figure 3:
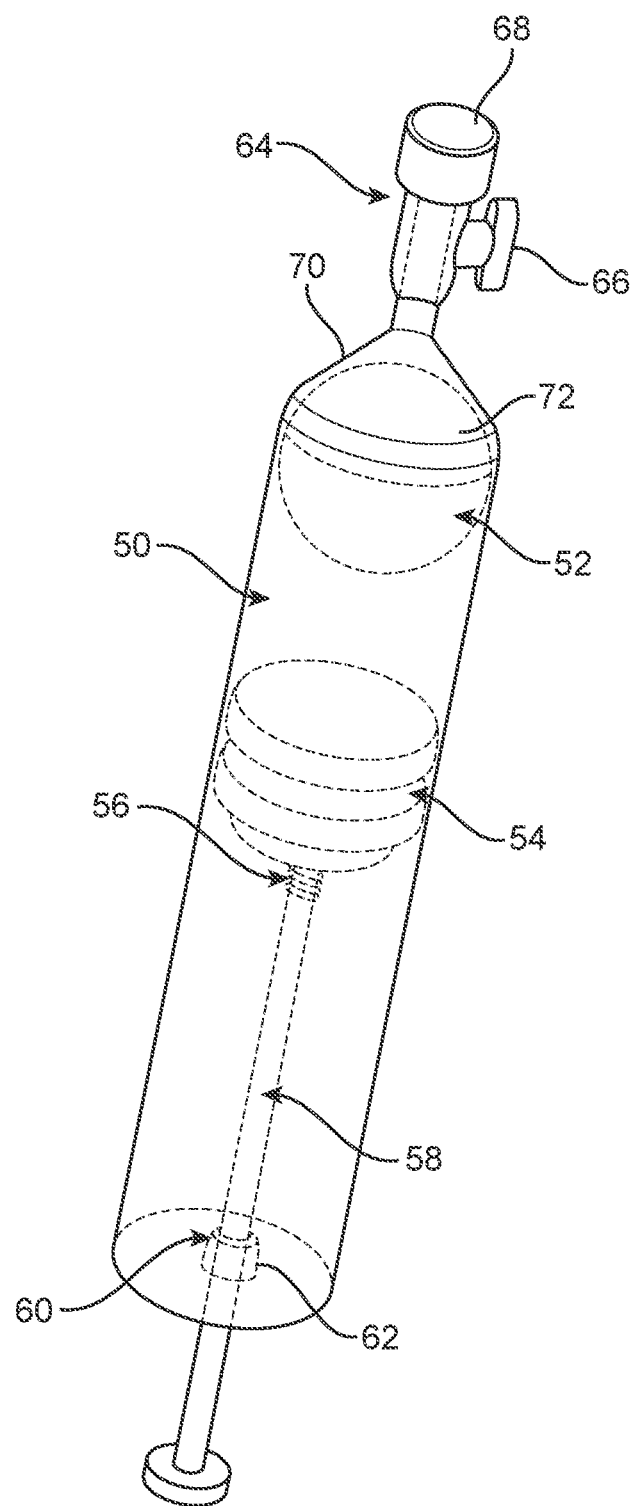
FIG. 3 shows a perspective view of another variation of the float separator assembly.

In yet another variation, a syringe or container tube 50, as shown in the perspective view of FIG. 3, may be used in a vacuum-drawn system for separating and then collecting the supernatant fraction. The container tube 50 is shown with the separator float 72 contained within the channel of the tube 50. The outer diameter 52 of the float 72 may be seen to form an annular channel, as described herein. A translatable plunger 54 may be slidably positioned within the channel and a pull rod 58 may be coupled to the plunger 54 via a plunger lock 56 attached to the plunger 54 on a side of the plunger 54 opposite to the float 72. A pull rod lock 60 may be integrated with the tube 50 at a distal surface of the tube 50 around a pull rod opening 62 through which the pull rod 58 may be translated. A Luer assembly 64 may be integrated with at a proximal end of the tube 50 along with a valve 66 and a cap or septum Luer 68 which may be used to seal the Luer 64.

As discussed previously, a cap may be removable to provide access for withdrawal while the use of a septum Luer 68 may enable the septum Luer 68 to remain in place, e.g., for introducing blood into the tube 50. After centrifugation, the septum Luer 68 may be optionally removed to allow for connection to a withdrawal syringe. Additionally, use of a septum Luer 68 may also obviate the use or need of a separate valve 66.

The proximal end of the tube 50 just below the Luer assembly 64 may also define an interface surface 70 which may be tapered or shaped to receive the float 72 in a corresponding manner to optimize the amount of the PRP layer which may be withdrawn from the tube 50.

Figure 4C:
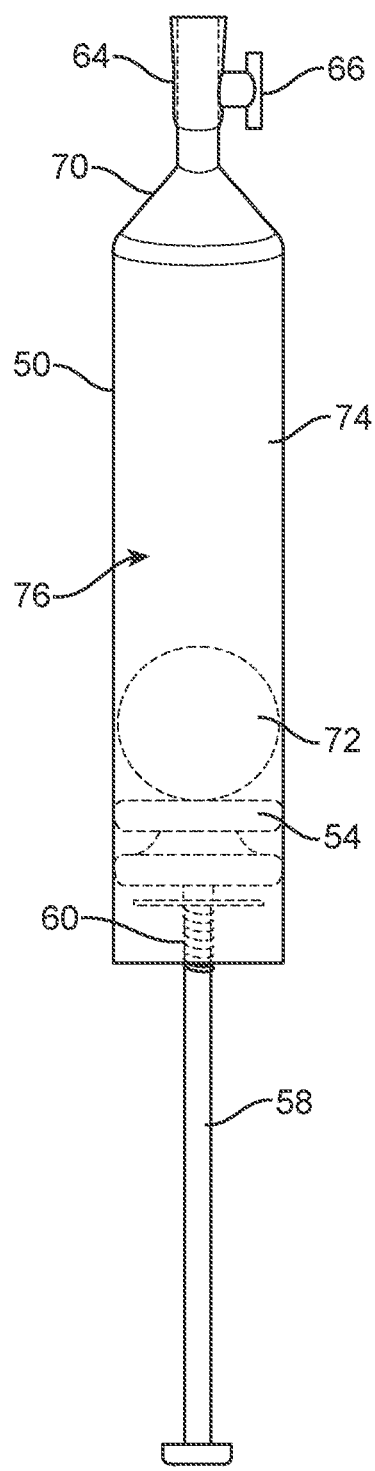

FIGS. 4A to 4G show side views of one variation for utilizing the container tube 50. As shown in FIG. 4A, the pull rod 58 may be pushed to move the plunger 54 and float 72 into an initial position where the float 72 is pushed into contact against the interface surface 70 of tube 50 prior to receiving whole blood. The tube 50 may be supplied preloaded with, e.g., anticoagulant or any other agent, contained within the channel. Having the tube 50 preloaded with anticoagulant would enable the blood to be drawn directly into the tube 50 without the need for additional processing. With the valve 66 closed, the pull rod 58 may be pulled or pushed to move the plunger 54 into a distal position within the tube 50, as shown in FIG. 4B. The float 72 may be seen as dropping through the channel 74 of the tube 50 along with the plunger 54. Because the valve 66 is closed, a vacuum may be formed within the tube 50. The pull rod 58 may be rotated partially about its longitudinal axis relative to the tube 50 and plunger 54 so as to lock a position of the pull rod 58 to the tube 50 and to prevent the plunger 54 from being moved back proximally in position due to the vacuum.

Figure 4D:
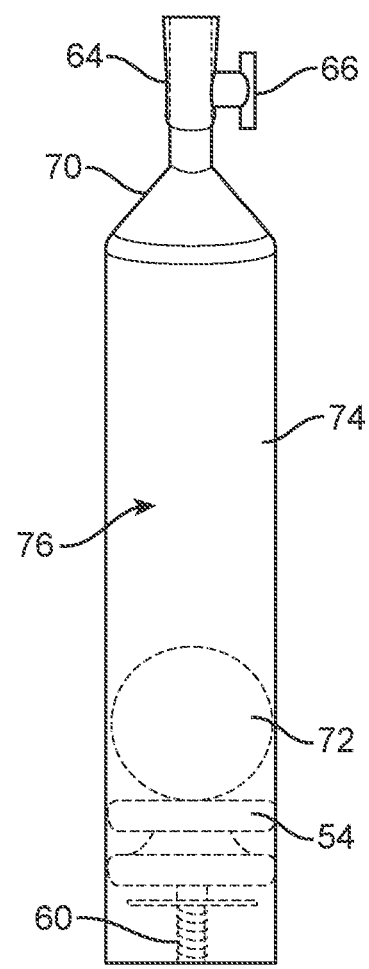

A syringe or blood line may be attached to the Luer 64 and the valve 66 may then be opened, as shown in FIG. 4C, allowing (whole) blood 76 to be drawn through the Luer 64 and into the channel 74 by the vacuum formed within the tube 50. Once the blood 76 has filled the channel 74 of tube 50, the valve 66 may then be closed again and the blood line disconnected and removed. As shown in FIG. 4D, the pull rod 58 may be decoupled or detached from the plunger lock 56 as well as from the pull rod lock 60 such that the pull rod 58 is fully removed so that the tube 50, float 72, and whole blood 76 may be centrifuged. With the whole blood 76 introduced within the channel 74 or tube 50, the float 72 may remain settled at its distal position prior to centrifuging the assembly.

Figure 4G:
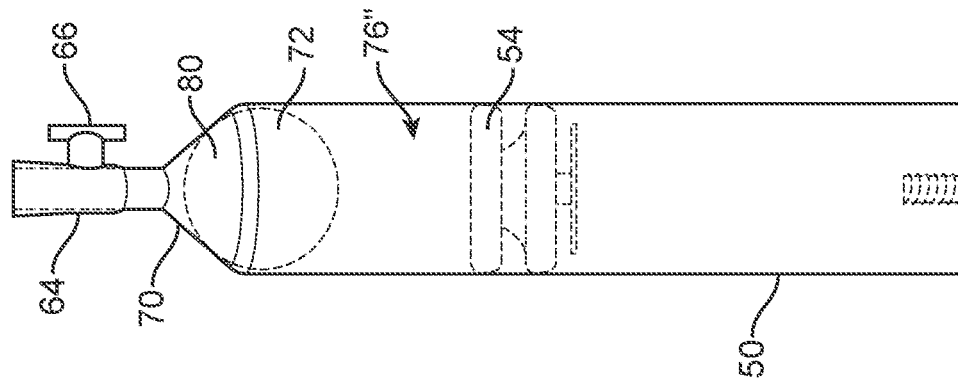
Figure 4F:
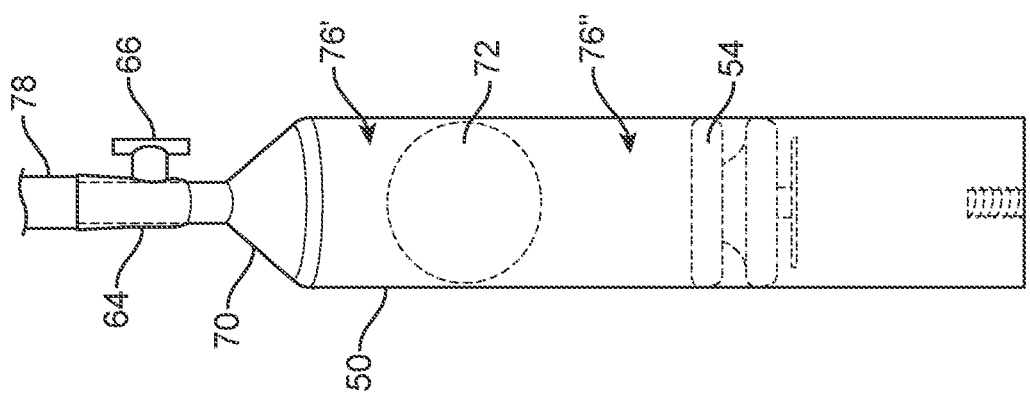
Figure 4E:
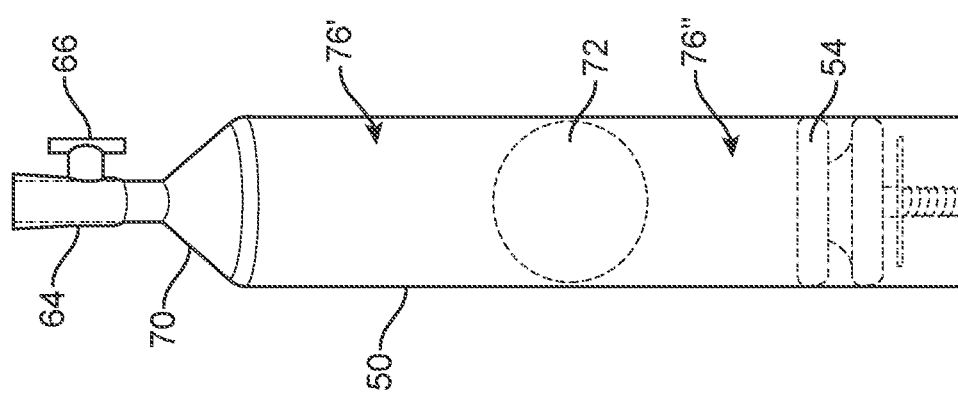

Once the tube 50 and its contents have been sufficiently centrifuged, the whole blood 76 may separate into its fractional components and the float 72 may alter its position within the channel 74 accordingly due to the differing densities of the individual fractional layers. The variation shown in FIG. 4E illustrates the float 72 at equilibrium positioned at the interface between a first layer, e.g., PRP layer 76', and a second layer, e.g., RBC layer 76". To effect removal of the PRP layer 76', a syringe or line 78 may be coupled to the Luer 64 and the valve 66 may then be opened to allow withdrawal of the PRP layer 76' through line 78 and as shown in FIG. 4F. The RBC layer 76" may remain between the plunger 54 and float 72 and the float 72 may remain at the interface of the PRP layer 76' and RBC layer 76" as the PRP layer 76' is withdrawn through Luer 64. As shown, both the float 72 and plunger 54 may accordingly move up through the channel 74. As the PRP layer 76' is fully withdrawn, as shown in FIG. 4G, the upper surface of the float 72 may come into contact against the interface surface 70 of the tube 50 so that the float 72 and interface surface 70 form a float interface 80 which may seal the tube 50 and prevent any further withdrawal through Luer 64. The RBC layer 76" may accordingly remain trapped between the lower surface of the float 72 and the plunger 54.

Due to the float 72 sealing against the RBC layer 76", even if the withdrawn PRP layer 76' were reintroduced back into the tube 50, the RBC layer 76" will remain contained beneath the float 72 and its volume unchanged.

Figure 5A:
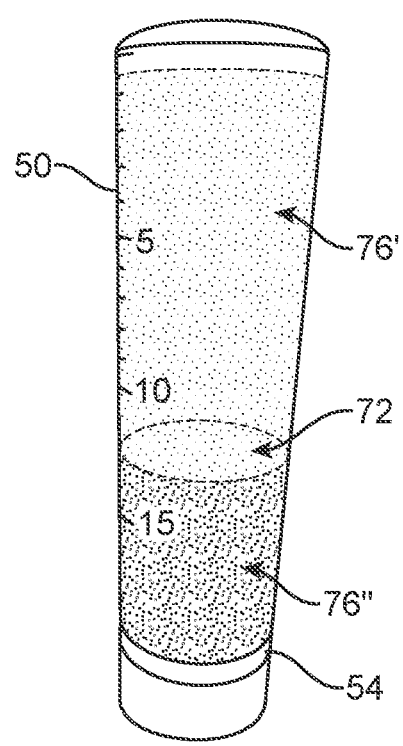
FIGS. 5A and 5B show perspective views of the float separator positioned between the separated blood components.
Figure 5B:
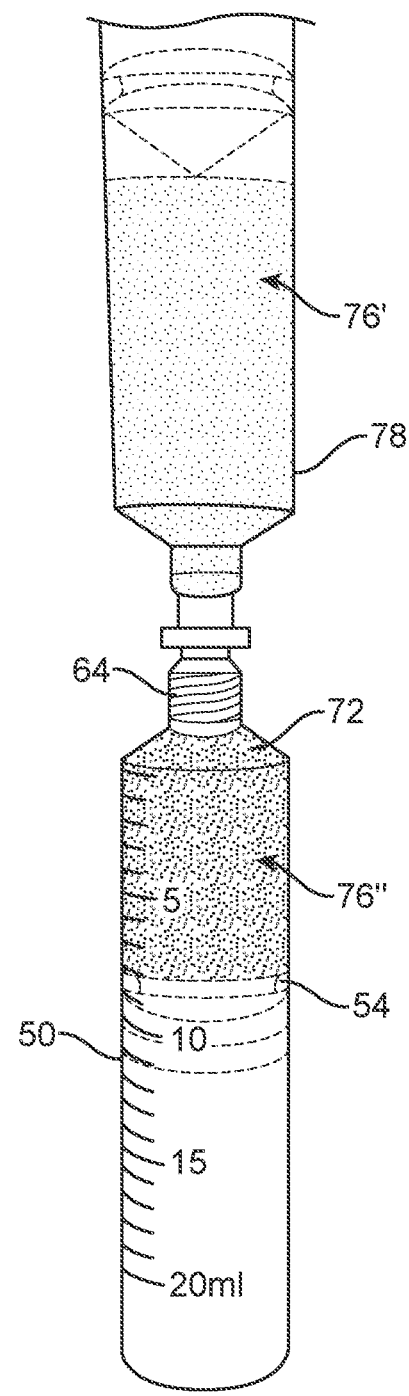

FIGS. 5A and 5B show another example of the resulting fractional layers 76', 76" with the float 72 positioned at equilibrium between the layers contained within the tube 50 after centrifugation. FIG. 5B shows syringe 78 coupled to the Luer 64 and the PRP layer 76' drawn into the syringe 78 while the RBC layer 76" remained trapped between the float 72 and plunger 54 within tube 50. Once the PRP layer 76' has been sufficiently withdrawn, the syringe 78 may be detached from Luer 64 for further processing and use leaving the RBC layer 76" remaining in the tube 50.

As discussed herein, the whole blood 76 may be subjected to a "hard spin" to obtain a buffy coat above the midline 34 of the float or anywhere along the float. A volume of the resulting platelet-poor plasma (PPP) which may form above the PRP layer 76' may be withdrawn from the tube 50. The buffy coat contained within the tube 50 may be re-suspended in the smaller remaining volume by pulling the remaining supernatant fluid back-and-forth within the syringe 78 several times with minimal shearing or frothing. A stop may be removably affixed to the tube 50 so that a distance between the float and the interface surface 70 of the tube 50 is fixed in order to define the volume of the supernatant fluid in which the buffy coat is resuspended to a preset amount. The buffy coat may then be re-suspended and withdrawn by removing the stop.

Figure 6:
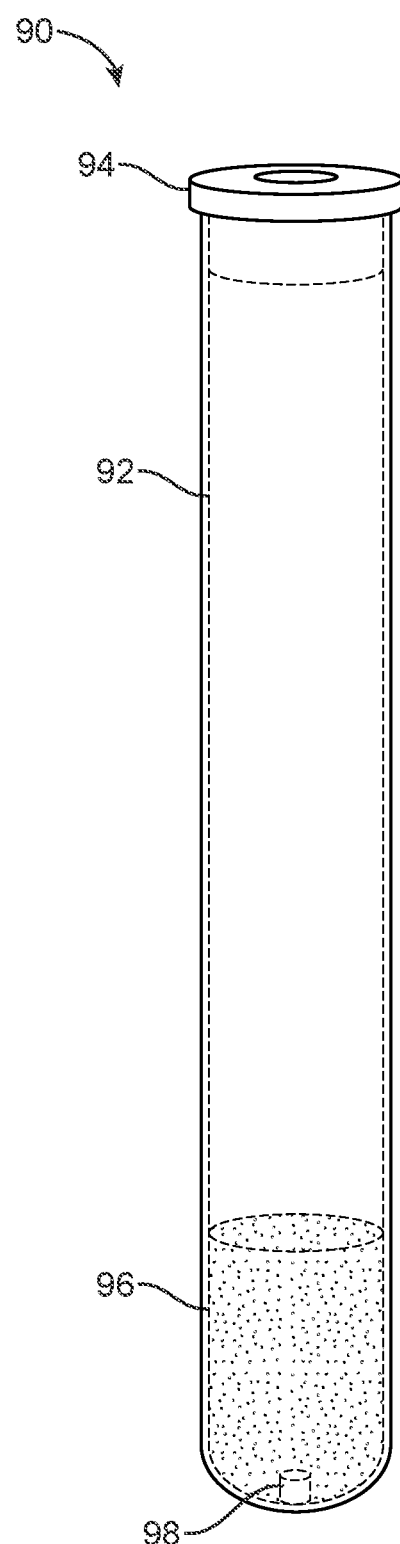
FIG. 6 shows a perspective view of a tube assembly which enables the float to be maintained in a secured configuration.

In yet another variation of a system that may be used to maintain the float 96 in a secured configuration particularly during shipping and handling, FIG. 6 illustrates a perspective view of a tube assembly 90 which enables the float 96 to be maintained in a secured configuration when the tube 92 may be filled with agents such as a volume of anticoagulant, e.g., ACD-A. The tube 92 may be sealed under vacuum with a septum 94 and may allow for blood to be drawn directly from the patient and into a tube 92 which may be preloaded with anticoagulant. The tube 92 may be fabricated from glass to prevent any potential issues with foreign agents leaching from the tube and into the enclosed volume of anticoagulant, e.g., during storage.

As shown, the float 96 may be enclosed within the tube 92 along with the volume of anticoagulant. However, the float 96 may potentially rise within the tube 92 due to density differences with the anticoagulant and the float 96 is desirably secured into an immobile position for shipping and handling. In this variation, the float 96 may be fabricated from any number of biocompatible materials, such as HDPE, and may have a density of, e.g., 1.03 to 1.07 or just under 1.04 in this variation. Because of the hardness of a glass tube 92, an external clamp may be inappropriate for securing a position of the float 96 within the tube 92. If the tube 92 were made from a plastic material, a clamp may be simply positioned over the external surface of the tube 92 in proximity to the float 96 such that the walls of the tube 92 deform slightly and compress upon the float 96 to maintain it in position and prevent its movement (as described in further detail below); however, applying a compressive force may not be feasible with a tube 92 made from a relatively harder material such as glass. The float 96 may accordingly have an attractive element 98, such as a magnet, integrated within the float 96 such as a distal end or portion of the float 96 in proximity to the distal end or bottom of the tube 92 interior. The attractive element 98 may be varied in dimension (e.g., 3.175 mm length and 3.175 mm diameter) and magnetic strength depending on the desired attractive force to retain the float 96 position.

The attractive element 98 may be embedded entirely within the float 96 to prevent direct contact with any fluids within the tube 92 or it may be configured to project beyond the surface of the float 96. A corresponding external attractive element 102 (described below) may be positioned along or against the exterior of the tube 92 in apposition to the attractive element 98 contained within or along the float 96, e.g., a removable external magnet positioned over the tube 92 or within or along packaging containing the tube 92. Because the external attractive element 102 is positioned externally of the tube 92, the external element 102 may be simply removed a distance from the tube 92 to sever the magnetic attraction between the elements and thereby release the position of the float 96 prior to or after receiving blood within the tube 92 so that the float 96 may be free to reposition itself accordingly within the tube 92.

Figure 7A:
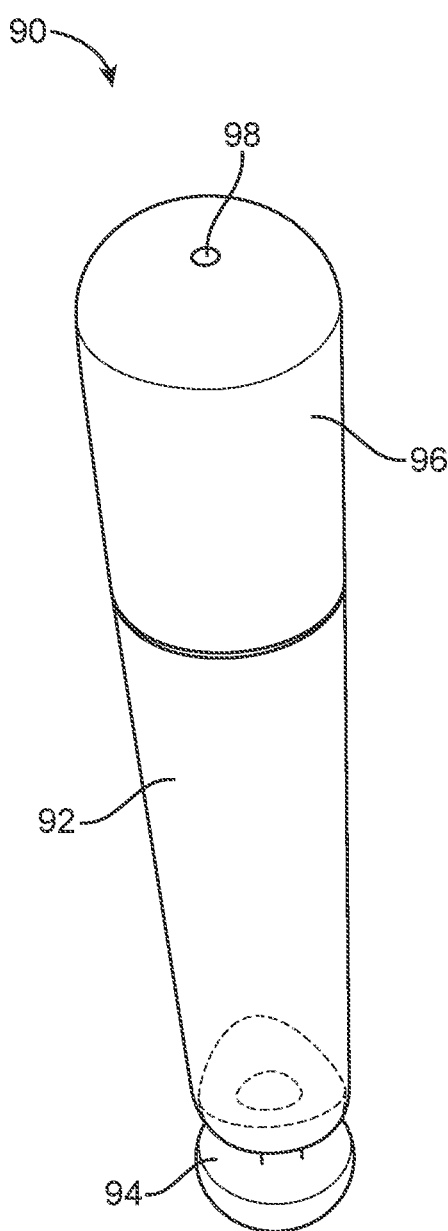
FIGS. 7A and 7B show perspective views of the tube with the float positioned within the bottom of the tube interior and of the float removed from the tube with the attractive element contained entirely within or along the float.
Figure 7B:
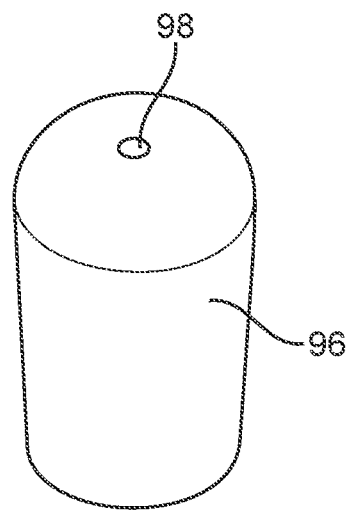

FIG. 7A illustrates a perspective view of the tube 92 with the float 96 positioned within the bottom of the tube interior with the attractive element 98 contained entirely within or along the float 96. FIG. 7B illustrates a perspective view of the float 96 removed from the tube 92 to show how the attractive element 98 may be positioned near a distal end or portion of the float 96 while remaining entirely embedded within.

Figure 8A:
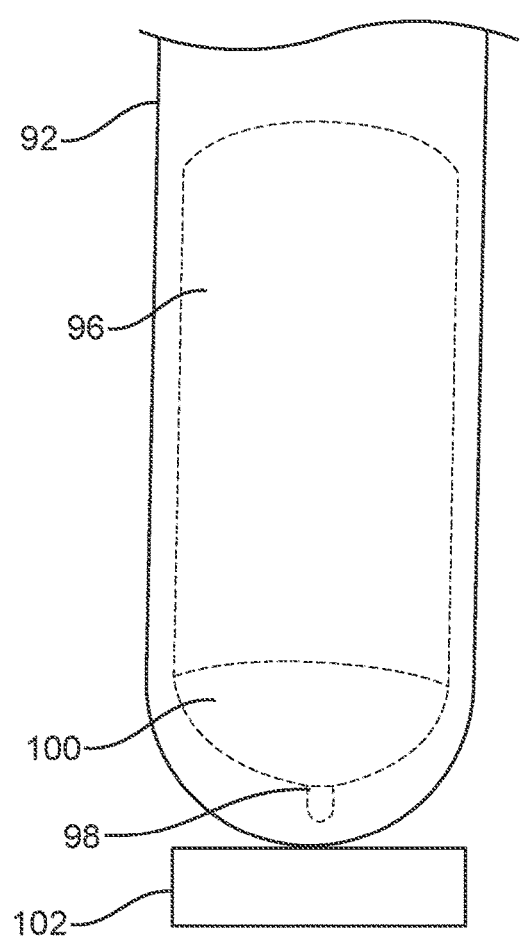
FIGS. 8A and 8B show side views of different embodiments of the float abutting against the bottom of the tube with the attractive element embedded within the float.
Figure 8B:
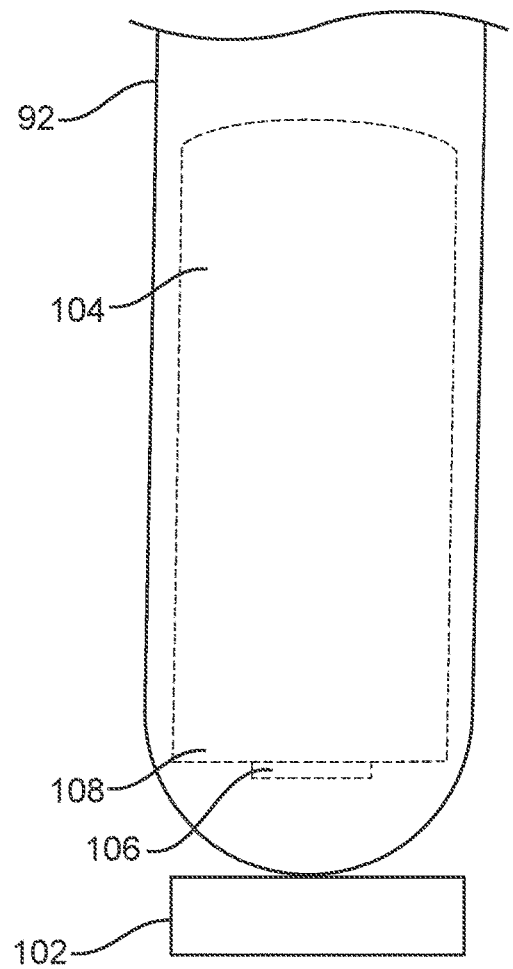

FIG. 8A shows a side view of the float 96 abutting against the bottom of the tube 92 with the attractive element 98 embedded within the float 96 and in proximity to the bottom of the tube 92. The external attractive element 102 is illustrated as being positioned externally of the bottom of tube 92 and in proximity to the float 96 and attractive element 98 such that the position of the float 96 is maintained securely within the tube 92. The bottom portion of the float 96 may be shaped with an interface surface 100 which is configured to mate closely in a corresponding manner with the interior of the bottom of tube 92. FIG. 8B shows another variation of the float 104 where the interface surface 108 may be configured in a non-conforming shape such as a flattened profile with the attractive element 106 embedded and still in proximity to the external attractive element 102, as shown.

Figure 9:
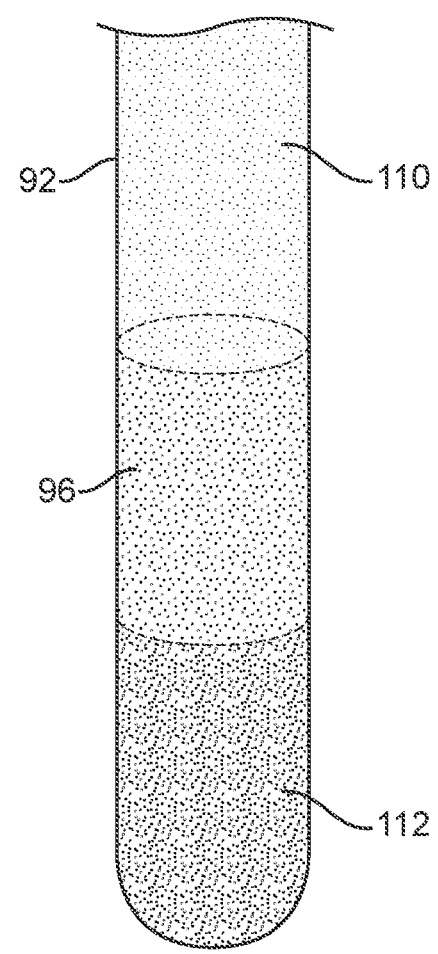
FIG. 9 shows a perspective view of the released float repositioned to separate the layer of PPP from RBC.

In use, the external attractive element 102 may be removed to allow for the float 96 to reposition itself during layer separation, as described herein. FIG. 9 shows a perspective view of the released float 96 repositioned to separate the layer of PPP 110 from RBC 112. Variations of the float 96 having attractive element 98 embedded within are intended to be utilized in any number of combinations with any of the floats described herein.

Figure 10:
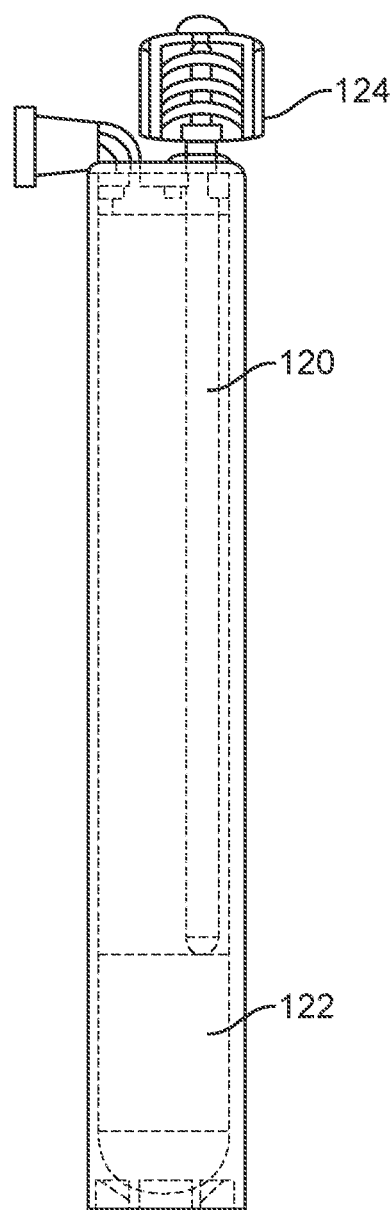
FIG. 10 shows a side view of a tube having a removable packaging post positioned to secure a position of the float within the tube.

In yet another variation which may be used with or without the attractive elements embedded within the float, a removable packaging post 120 may be incorporated within a cap 124, e.g., Luer cap, which may be removably attached to the opening of the tube, as shown in the side view of FIG. 10. The packaging post 120 may extend from the cap 124 and into the interior of the tube and into contact against the top surface of the float 122 to maintain the position of the float 122 during shipping and handling. When the tube is readied for use, the cap 124 and its extending packaging post 120 may be removed from the tube allowing for the float 122 to move within the tube interior. While removing the packaging post 120 may break a vacuum seal within the tube, the packaging post 120 may be used with any of the float variations described herein.

Figure 11:
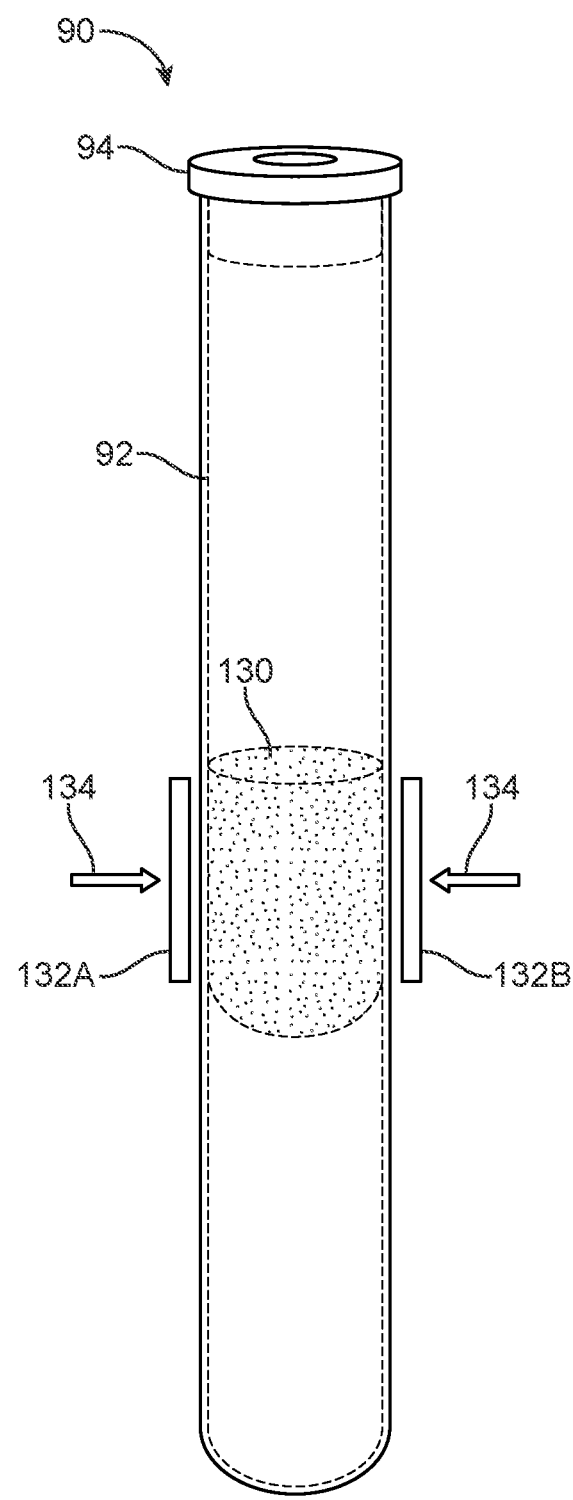
FIG. 11 shows a perspective view of a float maintained in position within the tube via a clamp or other external compressive mechanism.

In yet another variation for maintaining a position of the float 130 during shipping and handling, the tube 92 may be fabricated from a plastic material and a clamp or other compressive mechanism having one or more compressive members 132A, 132B may be simply positioned over the external surface of the tube 92 in proximity to the float 130, as shown in the perspective view of FIG. 11. The tube 92 may be vacuum sealed with septum 94 (with or without any Luer fittings) enclosing the tube 92 interior. The compressive members 132A, 132B of the clamp may be secured against the tube exterior to apply a compressive force 134 such that the walls of the tube 92 deform slightly and compress upon the float 130 to maintain it in position and prevent its movement prior to use. Compression of the float 130 may help to ensure that the float 130 remains in position within the tube 92 particularly if any anticoagulant is preloaded within the tube 92. The clamp may be removed prior to use or after blood introduction and before centrifugation.

Statements of the Disclosure include:

Statement 1: An apparatus for separating blood, comprising: a tube defining a channel and configured for receiving a quantity of blood; and a float contained within the tube and having a density which is predefined so that the float is maintained at equilibrium between a first layer formed from a first fractional component of the blood and a second layer formed from a second fractional component of the blood.

Statement 2: The apparatus of Statement 1, wherein the float defines a shape selected from the group consisting of spherical, ellipsoidal, and cylindrical shapes.

Statement 3: The apparatus of Statement 1 or Statement 2, wherein the float defines at least one tapered or slanted surface.

Statement 4: The apparatus as in any of Statements 1-3, wherein the float defines at least one non-orthogonal surface relative to a normal surface of the float.

Statement 5: The apparatus as in any of Statements 1-4, wherein the float has a density of 1.0 to 1.1 gram/ml.

Statement 6: The apparatus as in any of Statements 1-5, wherein the float has a density of 1.03 to 1.07 gram/ml.

Statement 7: The apparatus as in any of Statements 1-6, wherein the float has a density which is intermediate of the first layer comprised of a RBC layer and the second layer comprised of a PRP layer.

Statement 8: The apparatus as in any of Statements 1-7, wherein an outer diameter of the float is between 98 to 101% of the inner surface of the channel.

Statement 9: The apparatus as in any of Statements 1-8, wherein the float has a surface configured to retain a layer of red blood cells.

Statement 10: The apparatus as in any of Statements 1-9 wherein the float has a surface configured to inhibit a layer of red blood cells from adhering.

Statement 11: The apparatus as in any of Statements 1-10, further comprising an anticoagulant contained within the tube.

Statement 12: The apparatus as in any of Statements 1-11, wherein the density is further predefined to be maintained at equilibrium below a third layer formed from a third fractional component of the blood.

Statement 13: The apparatus as in any of Statements 1-12, wherein the density is further predefined to be maintained at equilibrium below a surface of a third layer formed from a third fractional component of the blood.

Statement 14: The apparatus of Statement 12 or Statement 13, wherein the third layer comprised of a buffy coat layer.

Statement 15: The apparatus as in any of Statements 1-14, further comprising a septum sealing a proximal end of the tube.

Statement 16: The apparatus as in any of Statements 1-15, wherein the tube is configured to radially expand relative to its longitudinal axis from a first diameter to an expanded second diameter, the float having a float diameter which is equal to or larger than the first diameter but smaller the expanded second diameter.

Statement 17: The apparatus as in any of Statements 1-16, further comprising a first attractive element embedded within the float.

Statement 18: The apparatus of Statement 17, further comprising a second attractive element positioned externally of the tube and in proximity to the first attractive element.

Statement 19: The apparatus as in any of Statements 1-18, further comprising a clamp configured to apply a compressive force upon an external surface of the tube in proximity to the float to secure a position of the float relative to the tube.

Statement 20: The apparatus as in any of Statements 1-19, further comprising a post which extends within an interior of the tube and into contact against a top surface of the float to maintain a position of the float within the tube.

Statement 21: The apparatus of Statement 20, wherein the post is incorporated within a cap removably attachable to an opening of the tube.

Statement 22: The apparatus as in any of Statements 1-21, wherein the float has a density which is predefined so that a midline of the float is maintained at equilibrium.

Statement 23: The apparatus as in any of Statements 1-22, wherein the float has a surface topography configured to substantially prevent platelet adhesion.

Statement 24: The apparatus as in any of Statements 1-23, wherein the float is configured to have a surface topography and surface tapered at an angle to substantially prevent platelet adhesion.

Statement 25: The apparatus as in any of Statements 1-24, wherein the float comprises a plurality of materials.

Statement 26: The apparatus as in any of Statements 1-25, wherein the float comprises a plurality of polymeric materials.

Statement 27: The apparatus as in Statement 26, wherein the float comprises a first polymeric material and a second polymeric material.

Statement 28: The apparatus as in Statement 26, wherein the first polymeric material and second polymeric material are present in a weight ratio effective to provide a density of 1.0 to 1.1 gram/ml.

Statement 29: The apparatus as in Statement 27 or Statement 28, wherein the first polymeric material and second polymeric material are present in a weight ratio effective to provide a density of 1.03 to 1.07 gram/ml.

Statement 30: The apparatus as in any of Statements 1-29, wherein the size and shape of the float remain substantially fixed.

Statement 31: The apparatus as in any of Statements 1-30, wherein the float does not comprise a fluid-swellable material.

Statement 32. The apparatus as in any of Statements 1-31, wherein the float does not comprise any protrusions.

Statement 33: The apparatus as in any of Statements 1-32, wherein the float has a surface topography and shape that substantially avoids damage to one or more platelets.

Statement 34: The apparatus as in any of Statements 1-33, wherein the float has a surface topography and shape that prevents damaging one or more platelets.

Statement 35: The apparatus as in any of Statements 9-34, wherein the layer of red blood cells has a thickness effective to substantially avoid damaging one or more platelets.

Statement 36: A method for separating blood, comprising: introducing a volume of blood into a channel of a tube which encloses a float having a density which is predefined; subjecting the tube to a centrifugation such that the blood separates into at least a first layer formed from a first fractional component of the blood and a second layer formed from a second fractional component of the blood, wherein the float is maintained at equilibrium between the first layer and the second layer.

Statement 37: The method of Statement 36, wherein the float defines a shape selected from the group consisting of spherical, ellipsoidal, and cylindrical shapes.

Statement 38: The method as in any of Statements 36-37, wherein the float defines at least one tapered or slanted surface.

Statement 39: The method as in any of Statements 36-38, wherein the float has a density of 1.0 to 1.1 gram/ml.

Statement 40: The method as in any of Statements 36-39, wherein the float has a density of 1.03 to 1.07 gram/ml.

Statement 41: The method as in any of Statements 36-40, wherein the float has a density which is intermediate of the first layer comprised of a RBC layer and the second layer comprised of a PRP layer.

Statement 42: The method as in any of Statements 36-41, wherein an outer diameter of the float is between 98 to 101% of the inner surface of the channel.

Statement 43: The method as in any of Statements 36-42, wherein subjecting the tube to a centrifugation further comprises retaining a layer of red blood cells upon a surface of the float.

Statement 44: The method as in any of Statements 36-43, wherein subjecting the tube to a centrifugation further comprises inhibiting adhesion of a layer of red blood cells upon a surface of the float.

Statement 45: The method as in any of Statements 36-44, further comprising introducing an anticoagulant within the tube.

Statement 46: The method as in any of Statements 36-45, further comprising subjecting the tube to a second centrifugation such that the blood further separates into a third layer formed from a buffy coat layer.

Statement 47: The method as in Statement 46 wherein the density of the float is further predefined to be maintained at equilibrium below the third layer.

Statement 48: The method as in any of Statements 46-47, further comprising removing a post extending within an interior of the tube which is vacuum sealed and into contact against a top surface of the float prior to introducing the volume of blood.

Statement 49: The method as in Statement 48, further comprising breaking a vacuum seal within the tube while removing the post from within the interior of the tube.

Statement 50: The method as in any of Statements 46-49, wherein subjecting the tube to a centrifugation comprises radially expanding the tube relative to its longitudinal axis from a first diameter to an expanded second diameter such that the float is free to migrate within the channel.

Statement 51: The method of Statement 50, further comprising stopping the centrifugation such that tube contracts from its expanded second diameter back to its first diameter and secures the float at its equilibrium position against the channel.

Statement 52: The method as in any of Statements 46-51, further comprising securing a position of the float within the tube via a first attractive element embedded within the float and a second attractive element positioned externally of the tube and in proximity to the first attractive element prior to subjecting the tube to the centrifugation.

Statement 53: The method as in any of Statements 46-51, further comprising securing a position of the float within the tube via a clamp configured to apply a compressive force upon an external surface of the tube in proximity to the float.

Statement 54: The method as in any of Statements 36-52, wherein a midline of the float is maintained at equilibrium.

Statement 55: A method for preparing a platelet rich plasma, comprising: providing an apparatus as in any of Statements 1-35 and a blood sample (e.g. whole blood); centrifuging the blood sample in the apparatus for a time and at a speed sufficient to separate the blood sample into a first phase and a second phase, wherein the first phase comprises red blood cells and the second phase comprises plasma; and removing a portion of the second phase to create a platelet rich plasma.

Statement 56: The method as in Statement 55, wherein the portion removed from the second phase comprises platelet poor plasma.

Statement 57: The method as in Statements 55-56, further comprising resuspending the platelet rich plasma.

Statement 58: The method as in Statements 55-57, wherein the float is maintained at equilibrium between the first phase and the second phase.

Statement 59: The method as in Statements 55-58, wherein the apparatus is centrifuged for a time and at a speed sufficient to separate the blood sample into a first phase, a second phase and a third phase.

Statement 60: A method for separating a biological sample, comprising: introducing a volume of blood into the apparatus as in any of Statements 1-36; subjecting the apparatus to a centrifugation such that the biological sample separates into a first phase and a second phase; wherein the float is maintained at equilibrium between the first phase and the second phase.

Statement 61: A method for separating blood, comprising: introducing a volume of blood into the apparatus as in any of Statements 1-36; subjecting the apparatus to a centrifugation such that the blood separates into at least a first layer formed from a first fractional component of the blood and a second layer formed from a second fractional component of the blood; wherein the float is maintained at equilibrium between the first layer and the second layer.

Statement 62: A method for treating, preventing or ameliorating a symptom associated with: acne; alopecia; pain; periodontal disease; periodontal defects; a chronic wound; diabetic foot ulcer; traumatic injury; scars; incontinence; and/or wrinkles, comprising administering a product produced by the method as in any of Statements 55-61, to a mammalian subject in need thereof.

Statement 63: A method for treating, preventing or ameliorating a symptom associated with: acne; alopecia; pain; periodontal disease; periodontal defects; a chronic wound; diabetic foot ulcer; traumatic injury; scars; incontinence; and/or wrinkles, comprising administering a product produced by any one of the methods described herein to a mammalian subject in need thereof.

Statement 64: A method for increasing, enhancing or promoting: hair growth; tissue healing; tissue regeneration; sexual wellness; bone growth; bone regeneration; and/or periodontal regeneration; comprising administering a product produced by the method as in any of Statements 55-61, to a mammalian subject in need thereof.

Statement 65: A method for increasing, enhancing or promoting: hair growth; tissue healing; tissue regeneration; sexual wellness; bone growth; bone regeneration; and/or periodontal regeneration; comprising administering a product produced by any one of the methods described herein to a mammalian subject in need thereof.

Statement 66: A composition comprising a product produced by the method as in any of Statements 55-61; and a cosmetically acceptable carrier.

Statement 67: A composition comprising a product produced by any one of the methods described herein; and a cosmetically acceptable carrier.

Statement 68: A pharmaceutical composition comprising a product produced by the method as in any of Statements 55-61; and a pharmaceutically acceptable carrier.

Statement 69: A pharmaceutical composition comprising a product produced by any one of the methods described herein; and a pharmaceutically acceptable carrier.

EXAMPLES

In one example utilizing the devices and methods described, samples of human blood were collected into tubes filled with an anticoagulant (ACD-A). Each of the tubes were spun at 3200 rpm (1500×g) for a period of 5 minutes in a swinging bucket centrifuge. The float contained within the collection tubes had a predefined density of 1.04 g/ml.

After spinning the blood samples into their constituent components, the collection tubes were inverted several times to resuspend the platelets and the harvested upper fractional layers. The volume of the whole blood introduced into the tubes, the volume of the PRP harvested, the relative baseline counts, and the fold increase and percentage recovered were recorded and calculated, as presented in the following TABLE 1.

TABLE 1

FOLD INCREASE/PERCENTAGE RECOVERY FROM BLOOD SAMPLES

| Spin Time (min) | Spin Speed (rpm) | Spin ×g | Fixed/ Swing Bucket | Whole Blood Vol. IN (ml) | PRP Vol. OUT (ml) | Baseline Ct. (×10e6) | PRP Ct. (×10e6) | Fold Increase | % Recovery |
|---|---|---|---|---|---|---|---|---|---|
| 5 | 3200 | 1500 | Swing | 10 | 5.8 | 124 | 206 | 1.66 | 96.35 |
| 5 | 3200 | 1500 | Swing | 10 | 6 | 124 | 154 | 1.24 | 74.52 |

As shown in TABLE 1 above, the use of the float having the predefined density of 1.04 g/ml proved to be effective in separating the component layers from whole blood for harvesting from the collection tubes.

The apparatus and methods disclosed above are not limited to the individual embodiments which are shown or described but may include combinations which incorporate individual features between the different variations. Modification of the above-described assemblies and methods for carrying out the invention, combinations between different variations as practicable, and variations of aspects of the invention that are obvious to those of skill in the art are intended to be within the scope of the claims.

What is claimed is:

1. An apparatus for separating blood, comprising:
 a tube defining a channel and configured for receiving a quantity of blood, wherein the channel is sealed at a proximal end of the tube by a septum;
 a float having no protrusions and contained within the tube such that the float is vacuum sealed within the channel via the septum, the float having a density which is predefined between 1.0 to 1.1 gram/ml so that the float is maintained at equilibrium between a first layer formed from a first fractional component of the blood and a second layer formed from a second fractional component of the blood, wherein the float further has a cylindrical body with a proximal portion of the float having an angled surface which is angled from about 2 to 10 degrees relative to a longitudinal axis of the float such that the angled surface has a surface topography selected to retain a layer of red blood cells upon the angled surface of the proximal portion of the float,
 wherein the channel defined by the tube is maintained under vacuum prior to receiving the quantity of blood wherein the float remains settled in a distal position within the tube under vacuum.

2. The apparatus of claim 1 wherein the float has a density of 1.03 to 1.07 gram/ml.

3. The apparatus of claim 1 wherein the float has a density which is intermediate of the first layer comprised of a RBC layer and the second layer comprised of a PRP layer.

4. The apparatus of claim 1 wherein an outer diameter of the float which contacts an inner surface of the channel is between 98 to 101% of the inner diameter of the channel.

5. The apparatus of claim 1 wherein the float has a smoothed or tapered surface configured to inhibit a layer of red blood cells from adhering.

6. The apparatus of claim 1 further comprising an anti-coagulant contained within the tube.

7. The apparatus of claim 1 wherein the density is further predefined to be maintained at equilibrium below a third layer formed from a third fractional component of the blood.

8. The apparatus of claim 1 wherein the density is further predefined to be maintained at equilibrium below a surface of a third layer formed from a third fractional component of the blood.

9. The apparatus of claim 8 wherein the third layer is comprised of a buffy coat layer.

10. The apparatus of claim 1 wherein the tube is configured to radially expand relative to its longitudinal axis from a first diameter to an expanded second diameter, the float having a float diameter which is equal to or larger than the first diameter but smaller the expanded second diameter.

11. The apparatus of claim 1 wherein the float has a density which is predefined so that a midline of the float is maintained at equilibrium.

12. The apparatus of claim 1 wherein the float comprises a plurality of materials.

13. The apparatus of claim 1 wherein the float comprises a plurality of polymeric materials.

14. The apparatus of claim 13 wherein the float comprises a first polymeric material and a second polymeric material.

15. The apparatus of claim 14 wherein the first polymeric material and second polymeric material are present in a weight ratio effective to provide a density of 1.0 to 1.1 gram/ml.

16. The apparatus of claim 14 wherein the first polymeric material and second polymeric material are present in a weight ratio effective to provide a density of 1.03 to 1.07 gram/ml.

17. The apparatus of claim 1 wherein the size and shape of the float remain fixed.

18. The apparatus of claim 1 wherein the float does not comprise a swellable material.

* * * * *